United States Patent
Kucharczyk et al.

(12)

(10) Patent No.: US 6,298,259 B1
(45) Date of Patent: Oct. 2, 2001

(54) COMBINED MAGNETIC RESONANCE IMAGING AND MAGNETIC STEREOTAXIS SURGICAL APPARATUS AND PROCESSES

(76) Inventors: John Kucharczyk, 1117 Marquette Ave., Apartment 1406, Minneapolis, MN (US) 55403; George T. Gillies, 4310 Beaver Creek Rd., Earlysville, VA (US) 22936-9590

( * ) Notice: Subject to any disclaimer, the term of this patent is extended or adjusted under 35 U.S.C. 154(b) by 0 days.

(21) Appl. No.: 09/174,189

(22) Filed: Oct. 16, 1998

(51) Int. Cl.[7] .................................................. A61B 5/05

(52) U.S. Cl. ..................... 600/411; 600/415; 600/417; 600/420; 600/429; 324/307; 324/309; 324/310; 606/130

(58) Field of Search .................................. 600/407, 410, 600/411, 417, 415, 420, 429; 606/130; 324/307, 309, 310

(56) References Cited

U.S. PATENT DOCUMENTS

| | | | |
|---|---|---|---|
| 4,173,228 | 11/1979 | Van Steenwyk et al. | 128/653 |
| 4,791,934 | 12/1988 | Brunnett | 128/653 |
| 4,869,247 | 9/1989 | Howard, III et al. | 128/303.1 |
| 5,042,486 | 8/1991 | Pfeiler et al. | 128/653 R |
| 5,078,140 | 1/1992 | Kwoh | 128/653.1 |
| 5,111,541 | 5/1992 | Wagner | 5/81.1 |
| 5,125,888 | 6/1992 | Howard et al. | 600/12 |
| 5,211,165 | 5/1993 | Dumoulin et al. | 128/653.1 |
| 5,218,964 | 6/1993 | Sepponen | 128/653.2 |
| 5,230,338 | 7/1993 | Allen et al. | 128/653 |

(List continued on next page.)

FOREIGN PATENT DOCUMENTS

| | | | |
|---|---|---|---|
| 0712606 | 5/1996 | (EP) | A61B/5/055 |
| 92/01362 | 7/1990 | (WO) | H05K/9/00 |

OTHER PUBLICATIONS

Ashpole, R.D., et al., "A New Instrument for Improved Accuracy of Stereotactic Depth Electrode Placement", *Journal of Neurosurgery*, 85, Technical note, 357–358, (Aug. 1996).

Black, P.M., et al., "Development and Implementation of Intraoperative Magnetic Resonance Imaging and Its Neurosurgical Applications", *Neurosurgery*, 41 (4), Special Technical Article, 831–845, (Oct. 1997).

Bootsveld, K., et al., "Localisation of Intracranial EEG Electrodes Using Three Dimensional Surface Reconstructions of the Brain", *European Radiology*, 4, 52–56, (1994).

Cares, H.L., et al., "Laboratory experience with a magnetically guided intravascular catheter system", *Journal of Neurosurgery*, 38 (2), 145–154, (Feb. 1973).

Cox, R.W., et al., "Real–Time Functional Magnetic Resonance Imaging", *Magnetic Resonance in Medicine* 33 (2), 230–236, (Feb. 1995).

(List continued on next page.)

*Primary Examiner*—Marvin M. Lateef
*Assistant Examiner*—Talaya James
(74) *Attorney, Agent, or Firm*—Mark A. Litman & Assoc. P.A.

(57) ABSTRACT

A magnetic stereotaxis system (MSS) is functionally integrated with a magnetic resonance imaging (MRI) system to provide a non-invasive, radiation-free modality for integrated MRI/MMS tracking and guiding of an interventional medical device. Shielding is provided between regions where the patient is moved so that magnetic fields from one procedure do not interfere with the function or materials used in the other procedure. A process is described where a patient is moved on a track from one procedural field to another procedural field with the shield available between different zones provides for the procedures. A computer is associated with the system to supervise performance of a variety of functions and procedures within the surgical environment.

19 Claims, 2 Drawing Sheets

U.S. PATENT DOCUMENTS

| | | | |
|---|---|---|---|
| 5,242,455 | 9/1993 | Skeens et al. | 606/130 |
| 5,255,680 | 10/1993 | Darrow et al. | 128/653.1 |
| 5,259,011 | 11/1993 | Petro | 378/4 |
| 5,271,400 | 12/1993 | Dumoulin et al. | 128/653.2 |
| 5,279,309 | 1/1994 | Taylor et al. | 128/782 |
| 5,300,080 | 4/1994 | Clayman et al. | 606/130 |
| 5,305,203 | 4/1994 | Raab | 364/413.13 |
| 5,307,808 | 5/1994 | Dumoulin et al. | 128/653.2 |
| 5,318,025 | 6/1994 | Dumoulin et al. | 128/653.2 |
| 5,339,812 | 8/1994 | Hardy et al. | 128/653.1 |
| 5,383,454 | 1/1995 | Bucholz | 128/653.1 |
| 5,410,287 | 4/1995 | Laskaris et al. | 335/216 |
| 5,445,166 | 8/1995 | Taylor | 128/897 |
| 5,474,564 | 12/1995 | Clayman et al. | 606/130 |
| 5,474,565 | 12/1995 | Trott | 606/144 |
| 5,483,961 | 1/1996 | Kelly et al. | 128/653.1 |
| 5,517,990 | 5/1996 | Kalfas et al. | 128/653.1 |
| 5,519,372 | 5/1996 | Palkovich et al. | 335/216 |
| 5,525,905 * | 6/1996 | Mohapatra et al. . | |
| 5,531,227 | 7/1996 | Schneider | 128/653.1 |
| 5,531,520 | 7/1996 | Grimson et al. | 382/131 |
| 5,553,112 | 9/1996 | Hardy et al. | 378/206 |
| 5,558,091 | 9/1996 | Acker et al. | 128/653.1 |
| 5,565,831 | 10/1996 | Dorri et al. | 335/216 |
| 5,590,653 | 1/1997 | Aida et al. | 128/653.2 |
| 5,638,819 | 6/1997 | Manwaring et al. | 128/653.1 |
| 5,654,864 | 8/1997 | Ritter et al. | 361/141 |
| 5,681,260 * | 10/1997 | Ueda et al. . | |
| 5,705,335 | 1/1998 | Hendry | 435/6 |
| 5,707,335 | 1/1998 | Howard et al. | 600/12 |
| 5,713,357 | 2/1998 | Meulenbrugge et al. | 128/653.2 |
| 5,715,822 | 2/1998 | Watkins et al. | 128/653.5 |
| 5,720,720 | 2/1998 | Laske et al. | 604/49 |
| 5,740,802 | 4/1998 | Nafis et al. | 128/653.1 |
| 5,779,694 | 7/1998 | Howard et al. | 604/891.1 |
| 5,783,943 * | 7/1998 | Mastandrea et al. | 324/318 |
| 5,851,182 * | 12/1998 | Sahadevan . | |
| 6,157,853 * | 12/2000 | Blume et al. | 600/426 |

OTHER PUBLICATIONS

Gilles, G.T., et al., "Magnetic Manipulation Instrumentation for Medical Physics Research", *Review of Scientific Instruments* 65 (3), 533–562, (Mar. 1994).

Hammer, B.E., et al., "MR–PET: Sub–Millimeter MR and PET Images in the Same Scanner", 1.

Hata, N., et al., "Development of a Frameless and Armless Stereotactic Neuronavigation System with Ultrasonographic Registration", *Neurosurgery*, 41 (3), Instrumentation Application, 608–614, (Sep. 1997).

Hilal, S.K., et al., "Magnetically Guided Devices for Vascular Exploration and Treatment: Laboratory and Clinical Investigations", *Radiology*, 113 (3), 529–540, (Dec. 1974).

Hilal, S.K., et al., "POD Catheter: A Means for Small Vessel Exploration", *Journal of Applied Physics 40* (3), 1 p., (Mar. 1, 1969).

Howard, M.A., et al., "Magnetically guided stereotaxis", *Advanced Neurosurgical Navigation*, Chapter 45, 549–556, (1999).

Kelly, P.J., "Minimally Invasive Stereotactic Neurosurgery: The State of the Art and Future Directions", *New York Medical Center*, Website: http://mcns10.med.nyu.edu/research/future.html, 1–8 p.

Miyamoto, A., et al., "Series Imaging in MELAS", *Neuroradiology 39* (6), 427–430, (Jun. 1997).

Molcho, J., et al., "Selective Cerebral Catheterization", *IEEE Transactions on Bio–Medical Engineering*, BME–17 (2), 134–140, (Apr. 1970).

Penn, R.D., et al., "Intravascular intracranial EEG recording. Technical note", *Journal of Neurosurg*, 38 (2), 239–243, (Feb. 1973).

Ram, W., et al., "Heart Catherterization in a Neonate bu Interacting Magnetic Fields: A New and Simple Method of Catheter Guidance", *Catherterization and Cardiovascular Diagnosis*, 22 (4), 317–319, (Apr. 1991).

Ryan, M.J., et al., "Frameless Sterotaxy with Real–Time Tracking of Patient Head Movement and Retrospective Patient–Image Registration", *Journal of Neurosurgery*, 85, 287–292, (Aug. 1996).

van den Elsen, P.A., et al., "Marker–Guided Multimodality Matching of the Brain", *European Radiology*, 4, 45–51, (1994).

* cited by examiner

COMBINED MAGNETIC RESONANCE IMAGING AND MAGNETIC STEREOTAXIS SURGICAL APPARATUS AND PROCESSES

BACKGROUND OF THE ART

1. Field of the Invention

The present invention relates to surgical theaters, surgical procedures and apparatus for performing surgical procedures which combine magnetic resonance imaging and magnetic stereotaxis guidance or movement of medical devices or materials. The invention also relates to the design, construction and use of a neurosurgical theater where a magnetic surgery system (MSS) is functionally integrated with a magnetic resonance imaging (MRI) system so that MRI-guided, MSS-directed diagnostic and/or therapeutic procedures may be performed within the theater.

2. Field of the Invention

The concept of administering minimally invasive therapy, including minimally invasive drug delivered therapy follows recent trends in medical and surgical practice towards increasing simplicity, safety, and therapeutic effectiveness. Image-guided, minimally invasive therapies have already superseded conventional surgical methods in several procedures. For example, transvascular coronary angioplasty is often now an alternative to open-heart surgery for coronary artery bypass, and laparascopic cholecystectomy is often an alternative to major abdominal surgery for gall bladder removal. The use of the less invasive techniques has typically reduced hospital stays by 1–2 weeks and the convalescence periods from 1–2 months to 1–2 weeks.

While endoscopic, arthroscopic, and endovascular therapies have already produced significant advances in health care, these techniques ultimately suffer from the same limitation. This limitation is that the accuracy of the procedure is "surface limited" by what the surgeon can either see through the device itself or otherwise visualize (as by optical fibers) during the course of the procedure. That is, the visually observable field of operation is quite small and limited to those surfaces (especially external surfaces of biological masses such as organs and other tissue) observable by visible radiation, due to the optical limitations of the viewing mechanism. MR imaging, by comparison, overcomes this limitation by enabling the physician or surgeon to non-invasively visualize tissue planes and structures (either in these planes or passing through them) beyond the surface of the tissue under direct evaluation. Moreover, MR imaging enables differentiation of normal from abnormal tissues, and it can display critical structures such as blood vessels in three dimensions. Prototype high-speed MR imagers which permit continuous real-time visualization of tissues during surgical and endovascular procedures have already been developed. MR-guided minimally invasive therapy is expected to substantially lower patient morbidity because of reduced post-procedure complications and pain. The use of this type of procedure will translate into shorter hospital stays, a reduced convalescence period before return to normal activities, and a generally higher quality of life for patients. The medical benefits and health care cost savings are likely to be very substantial.

A specific area where research is moving forward on advances of this type is in the treatment of neurological disorders. Specifically, the advent of new diagnostic and therapeutic technologies promises to extend the range of application and the utility of intracerebral drug delivery procedures and thus possibly advance the efficacy of existing and/or planned treatments for various focal neurological disorders, neurovascular diseases and neurodegenerative processes. Currently, when the standard procedure requires neurosurgeons or interventional neuroradiologists to deliver drug therapy into the brain, the drug delivery device, such as a catheter, must either be passed directly through the intraparenchymal tissues to the targeted region of the brain, or guided through the vasculature until positioned properly. An important issue in either approach is the accuracy of the navigational process used to direct the movement of the drug delivery device. In many cases, the physical positioning of either part or all of the catheter's lumen within the brain is also important as, for example, in situations where a drug or some other therapeutic agent will be either infused or retroperfused into the brain through the wall or from the tip of the catheter or other drug delivery device.

New technologies like intra-operative magnetic resonance imaging and nonlinear magnetic stereotaxis, the latter discussed by G. T. Gillies, R. C. Ritter, W. C. Broaddus, M. S. Grady, M. A. Howard III, and R. G. McNeil, "Magnetic Manipulation Instrumentation for Medical Physics Research," *Review of Scientific Instruments*, Vol.65, No.3, pp.533–562 (March 1994), as two examples, will likely play increasingly important roles here. In the former case, one type of MR unit is arranged in a "double-donut" configuration, in which the imaging coil is split axially into two components. Imaging studies of the patient are performed with this system while the surgeon is present in the axial gap and carrying out procedures on the patient. A second type of high-speed MR imaging system combines high-resolution MR imaging with conventional X-ray fluoroscopy and digital subtraction angiography (DSA) capability in a single hybrid unit. These new generations of MR scanners are able to provide the clinician with frequently updated images of the anatomical structures of interest, therefore making it possible to tailor a given interventional procedure to sudden or acute changes in either the anatomical or physiological properties of, e.g., a part of the brain into which a drug agent is being infused.

Nonlinear magnetic stereotaxis is the image-based magnetically guided movement of a catheter or some other form of a (temporary or lermanent) implant directly through the bulk brain tissues or along tracts within the neurovasculature or elsewhere within the body. Electromagnets or permanent magnets are used to magnetically steer the implant, giving (for example) the neurosurgeon or interventional neuroradiologist the ability to guide the object along a particular path of interest. (The implant might be either magnetically and/or mechanically advanced towards its target, but is magnetically steered, in either case. That is, magnetic fields and gradients are used to provide torques and forces (including linear forces) to orient or shift the position of the implant or device, with a mechanical pushing force subsequently providing none, some, or all of the force that actually propels the implant or device. Additional force may be provided magnetically, hydraulically or by some other force means.) The implant's position is monitored by biplanar fluoroscopyor some other non-invasive visualization or imaging method, and its location is or can be indicated on a computerized atlas of brain images derived from a pre-operative MR scan. Among other applications, the implant might be used to tow a pliable catheter or other drug delivery device to a selected intracranial location through the brain parenchyma or via the neurovasculature. Magnetic manipulation of catheters and other probes is well documented in research literature. For example, Cares et al. (J. Neurosurg, 38:145, 1973) have described a magnetically guided microballoon released by RF induction heating, which was used to occlude experimental intracranial aneurysms. More recently, Kusunoki et al. (Neuroradiol 24: 127, 1982) described a magnetically controlled catheter with cranial balloon useful in treating experimental canine aneurysms. Ram and Meyer (Cathet. Cardiovas. Diag.22:317, 1991) have described a permanent magnet-tipped polyurethane angiography catheter useful in cardiac interventions, in particular intraventricular catheterization in neonates.

U.S. Pat. No. 4,869,247 teaches the general method of intraparenchymal and other types of magnetic manipulation, and U.S. Pat. Nos. 5,125,888; 5,707,335; and 5,779,694 describe the use of nonlinear magnetic stereotaxis to maneuver a drug or other therapy delivery catheter system within the brain. U.S. Pat. No. 5,654,864 teaches a general method of controlling the operation of the multiple coils of a magnetic stereotaxis system for the purpose of maneuvering an implant to precisely specified locations within the body.

Both of these technologies offer a capability for performing image-guided placement of a catheter or other drug delivery device, thus allowing drug delivery directly into selected brain tissues via infusion through the walls of the catheter or outflow from the tip of the catheter. In the case of drug delivery directly into the brain tissues, the screening of large molecular weight substances by the endothelial blood-brain barrier can be overcome. In the case of infusions into specific parts of the cerebrovasculature, highly selective catheterizations can be enabled by these techniques. In either case, however, detailed visual images denoting the actual position of the drug delivery device within the brain would be extremely useful to the clinician in maximizing the safety and efficacy of the procedure. The availability of an MR-visible drug delivery device combined with MR-visible drug agents would make it possible to obtain near real-time information on drug delivery during interventional procedures guided by non-linear magnetic stereotaxis. Drug delivery devices, such as catheters, that are both MR-visible and radio-opaque could be monitored by at least two modalities of imaging, thus making intra-operative verification of catheter location possible during nonlinear magnetic stereotaxis procedures. (Intra-operative MR assessment might require the temporary removal of the magnetic tip and/or any other magnetic or magnetic responsive component or element of the drug delivery catheter and interruption of the magnetic stereotaxis procedure to image the patient.).

The geometry and magnetic strength of the magnetic tip will depend upon the particular type of catheter or medical device with which the tip is being used. In a preferred embodiment, the tip would have as small a maximum dimension as would be consistent with maintaining sufficient magnetic dipole moment to couple satisfactorily to the external magnetic fields and gradients used to apply torques and forces to the tip for the purpose of steering or moving the catheter or other medical device. Typical sizes of the tip have ranged from a few tenths of a millimeter to several millimeters in maximum dimension in the various exploratory versions of such devices that have been studied to date. To that end, the tip might be made of a permanently magnetic or magnetically permeable material, with compounds of Nd—B—Fe being exemplary, as well as various iron alloys (ferrites and steel alloys). The magnetic tip may be fixed to the distal end of the catheter in any number of ways, depending in part upon the method of use of the catheter, the specific type of catheter, the procedures and the use of the catheter. In one design, the magnetic tip might simply be a small spherical or oblate spheroid of magnetic material (e.g., having a geometry where the semi-major axis is from 1.1 to 3 times longer, preferably from 1.5 to 2.0 or 2.5 times longer than the semi-minor axis). The magnetic tip may be originally fixed to the distal end of the catheter or medical device or passed through the length of the catheter so that it abuts against the internal distal end of the catheter (as a foot would abut the end of a sock). As noted, the magnetic tip may be fixed in place either on the inside, outside or embedded within the composition of the distal end of the catheter or medical device. In a preferred embodiment, the magnetic tip may be thermally, solubly, mechanically, electronically or otherwise removably attached to and separable from the distal end of the catheter or medical device. For instance, a heat soluble link is taught in U.S. Pat. No. 5,125,888.

In still another embodiment, the magnetic tip would constitute a plug in the end of an otherwise open-ended catheter, and the tip might either have an open bore along its axis, a plurality of open bores along its axis, or a single or plural configuration of holes along the side of the magnetic tip, any of which openings would be used to facilitate drug delivery from the catheter or to serve as an exit port for the delivery of some other therapy or device into a body part, such as the parenchymal tissues and/or the cerebrovasculature of the brain. Alternatively, the magnetic tip might simply constitute a solid plug that seals the end of the catheter. The distal end of the catheter at which the magnetic tip is placed must be configured such that axial forces and torques applied by either magnetic fields and gradients or by a guide wire internal to the catheter allow said distal end and magnetic tip to be propelled towards a target site within the body, and to do so without said distal end and magnetic tip separating from each other in an inappropriate way and/or at an undesired time or under undesired circumstances. If the magnetic tip must be removed, or detached and removed, for example, prior to MR imaging of the patient, such a procedure could be accomplished by the method taught in U.S. Pat. No. 5,125,888; 5,707,335; and 5,779,694, which call for dissolving a heat separable link between the tip and the catheter by a pulse of radio-frequency energy. An alternative means of removing the magnetic tip is discussed by M. A. Howard et al. in their article, "Magnetically Guided Stereotaxis," in Advanced Neurosurgical Navigation, edited by E. Alexander III and R. J. Maciunas (Thieme Medical Publisher, New York, 1998), which calls for withdrawing the magnetic tip from along the inside of the catheter that it has just steered into place within the body. Without removal of the magnetic tip from the catheter, whole body magnetic forces might be produced on it by the field of the MR imaging system, and these could cause undesired movement of the catheter within the body.

In the treatment of neurological diseases and disorders, targeted drug delivery can significantly improve therapeutic efficacy, while minimizing systemic side-effects of the drug therapy. Image-guided placement of the tip of a drug delivery catheter directly into specific regions of the brain can initially produce maximal drug concentration close to some targeted loci of tissue receptors following delivery of the drug. At the same time, the limited distribution of drug injected from a single catheter tip presents other problems. For example, the volume flow rate of drug delivery must be very low to avoid indiscriminate hydrodynamic damage or other damage to brain cells and nerve fibers. Delivery of a drug from a single point source may also limit the distribution of the drug by decreasing the effective radius of penetration of the drug agent into the surrounding tissue receptor population. Positive pressure infusion, i.e., convection-enhanced delivery of drugs into the brain, as taught by U.S. Pat. No. 5,720,720 may overcome the problem of effective radius of penetration. Also, U.S. patent application Ser. No. 08/857,043, filed on May 15, 1997 and titled "Method and Apparatus for Use with MR Imaging" describes a technology invented in-part by one of the present inventors comprising a method for observing the delivery of material to tissue in a living patient comprising the steps of a) observing by magnetic resonance imaging a visible image within an area or volume comprising tissue of said living patient, the area or volume including a material delivery device, b) delivering at least some material by the material delivery device into the area or volume comprising tissue of a living patient, and c) observing a change in property of said visible image of the area or volume comprising tissue of a living patient while said material delivery device is still present within the area or volume. This process, including the MRI visualization, is performed in approximately or actually real time, with the clinical procedure being guided by the MRI visualization.

Research on magnetic catheterization of cerebral blood vessels generally has focused on design of transvascular devices to thrombose aneurysms, to deliver cytotoxic drugs to tumors, and to deliver other therapies without the risks of major invasive surgery. Examples of such studies include Hilal et al (J. Appl. Phys. 40:1046, 1969), Molcho et al (IEEE Trans. Biomed. Eng. BME-17, 134, 1970), Penn et al (J. Neurosurg. 38:239, 1973), and Hilal et al (Radiology 113:529,1974). U.S. Pat. Nos. 4,869,247, 5,654,864, 5,125,888, 5,707,335 and 5,779,694 describe processes and apparatus for the use of magnetic stereotaxis for the manipulation of an object or implant which is moved into position within a patient, particularly within the cranial region and specifically within the brain but in principle elsewhere in the body also. These patents do no not involve any contemplation of real time visualization of drug distribution within the brain, especially by MRI. It should be noted that the potential exists for interactive interference between the two systems, magnetic resonance imaging and magnetic stereotaxis, particularly where fine images are being provided by a system based on magnetic microcoils, especially as described in U.S. patent application Ser. No. 08/916,596, filed on Aug. 22, 1997, which is incorporated herein by reference for its disclosure of the design, construction, structure and operation of such coils and such catheters in MR-guided procedures.

A source of drug delivery can be effected by devising a multi-lumen catheter with multiple drug release sources that effectively disperse therapeutic drug agents over a brain region containing receptors for the drug, or over an anatomically extensive area of brain pathology. A preferred type of structure is described in U.S. patent application Ser. No. 08/916,596, filed on Aug. 22, 1997, but other devices which are described in the background of the art in that application could also be used in the practice of the present invention.

The present invention describes methods for exploiting interactive interference between magnetic resonance imaging systems and magnetic stereotaxis systems. Both modalities rely on the creation of large external magnetic fields to function as designed. The magnetic field and field gradients of the magnetic stereotaxis system are used to steer an implant within the body, and especially within the brain, while the magnetic fields of the magnetic resonance imager are used to create images of the planes of tissue within the patient's body. The magnetic fields of either one of these systems/devices can perturb the size and shape (and, therefore, the function) of the fields of the other device. It is unlikely that a clinical configuration of these systems/devices would be purposely arranged so as to cause direct interference via interaction of the fields. However, a far more likely danger is that the magnetic tip of the implanted catheter or other MSS-guided device will experience bulk-body forces and torques if the patient is placed in the MR and is subjected to the resulting magnetic field produced during the course of its functioning. Such a field could very easily cause the magnetically-tipped implant to move away from the location into which it was navigated by the clinician operating the magnetic stereotaxis system. This might produce a dangerous situation for the patient and, hence, care must be taken to insure that the magnetic tip is either removed from the catheter in the patient prior to MR imaging, or that it is otherwise deactivated or made impervious to the effects of non-MSS fields to which it might be subjected. Moreover, the presence of a relatively large magnetic dipole in the patient's body, as might arise from the presence of the magnetic tip of the implanted catheter, would create artifacts in the MR images.

Neurosurgical procedures require precise anatomic localization of normal and abnormal tissues. Present systems of image-guided neurosurgery include framed and frameless technologies, which typically use images acquired preoperatively to create a three-dimensional space on which the surgical navigation is based. Framed systems use externally applied frames to establish the fiducials for navigation, whereas frameless systems use optical, electromagnetic, or ultrasound sensors and/or mechanical anus to identify anatomical locations and/or to track the position of surgical tools and instruments during surgical procedures. Some systems of frameless stereotaxis also attempt to use natural anatomical features of the head as reference points in the navigation process.

A variety of framed and frameless imaging and therapy delivery systems have been described in the art, representative examples of which are as follows:

U.S. Pat. No. 4,791,934 to Brunnett discloses a system in which a CT scan is acquired at one location, and is digitally stored in a computer. At a second location, the patient undergoes X-ray imaging, which is also stored in a computer. The X-ray image is then registered with the CT image in 3 dimensions to enable a surgeon to plan a best trajectory for a biopsy needle. U.S. Pat. No. 5,078,140 to Kwoh discloses an imaging device-aided robotic stereotaxis system, wherein an imaging system provides information about a body structure to a computer which controls a robotic arm which orients the surgical devices. U.S. Pat. No. 5,242,455 to Skeens and Miketic and U.S. Pat. No. 5,305,203 to Raab disclose methods for stereotactic placement of probes into a body region utilizing an imaging system, wherein the mechanical control system for placing the probe is imaged within the reference images of the body. U.S. Pat. Nos. 5,339,812 and 5,553,112 to Hardy et al. disclose(s) an image-based model for the planning and delivery of therapy to the body, wherein MRI or CT imaging data are used to provide three-dimensional stereotactic coordinates to guide anatomically targeted therapy. U.S. Pat. No. 5,309,923 to Kormos et al. and U.S. Pat. No. 5,517,990 to Kalfas et al. disclose a stereotaxy wand and tool guide, wherein a trajectory and location of the wand are superimposed on a diagnostic image on a monitor.

U.S. Pat. No. 5,230,338 to Allen et al. discloses an interactive image-guided system for displaying images corresponding to the placement of a surgical probe in the body. U.S. Pat. No. 4,173,228 to Van Steenwyk et al., and U.S. Pat. No. 5,042,486 to Pfeiler et al. disclose medical probes wherein electromagnetic signals are propagated between one antenna on the tip of the probe inserted into a body region and several antennae outside the body. The position and orientation of the probe tip are determined from the signals transmitted between said antennae. U.S. Pat. No. 5,211,165 to Dumoulin et al., U.S. Pat. No. 5,255,680 to Darrow and Dumoulin, U.S. Pat. No. 5,307,808 to Dumoulin et al., and U.S. Pat. No. 5,318,025 to Dumoulin et al. additionally disclose a tracking system in which radiofrequency signals emitted by an invasive device, such as a catheter, are detected and used to measure the device's position and orientation in a patient. Localization of devices in situ is achieved by transmitter radiofrequency coils positioned at its distal end, which are detected by receiver radiofrequency coils positioned around the imaging volume of interest. The position of the device, as determined by the tracking system, is superimposed upon independently acquired diagnostic images. U.S. Pat. No. 5,383,454 to Bucholz discloses a system for indicating a position of a tip of a probe which is positioned within an object on images of the object, wherein a computer employing translational software translates the position of the tip of said probe into a coordinate system corresponding to the coordinate system of the cross-sectional images.

U.S. Pat. No. 5,279,309 to Taylor et al. and U.S. Pat. No. 5,445,166 to Taylor disclose a system for positioning an object at a target location in a body, wherein a computer determines a surgical plan. U.S. Pat. No. 5,558,091 to Acker et al. discloses a system utilizing magnetic fields, wherein the position and orientation of probes within the magnetic fields can be determined within a body. U.S. Pat. No. 5,218,964 to Sepponen discloses a method for providing reference markers in MR images, wherein during MR imaging of a region of the body electron spin resonance energy is supplied to the reference markers to amplify the MR signal by dynamic nuclear polarization. U.S. Pat. No. 5,474,565 to Clayman and Nguyen discloses a method of performing a neurological procedure on a human, wherein an image is obtained of the patient's head, the patient is moved to the operating room, and the imaging data is used in conjunction with the cerebral instrument guide frame to guide one or more medical instruments.

U.S. Pat. No. 5,590,653 to Aida et al. discloses an ultrasonic wave medical treatment apparatus which can be used under MR imaging guidance. In this invention the ultrasonic wave applicator is incorporated into a surface coil for taking MR images. U.S. Pat. No. 5,483,961 to Kelly and Goerss discloses a magnetic field digitizer for stereotactic surgery. U.S. Pat. No. 5,654,864 to Ritter et al. discloses a control method for a magnetic stereotaxis system whereby a computer can control the operation of multiple superconducting magnetic coils to guide a magnetic object based on stored preoperative images and interoperative fluoroscopic images. U.S. Pat. No. 5,705,335 to Howard et al. discloses an MSS treatment delivery apparatus comprising a magnetic object and a treatment carrier device which is connected by a heat-sensitive biodegradable connector link to the magnetic object. In the method of this invention, a robotically moved electromagnet or multicoil electromagnet system moves the magnetic object within the body to a target location determined by a clinician-operated computer.

U.S. Pat. No. 5,713,357 to Meulenbrugge et al. discloses an MR imaging system in close physical proximity to an X-ray device, to enable the patient to more easily undergo both MR imaging and X-ray imaging. A method of minimizing incompatibility between the MR imager and the X-ray device is provided by using a solid-state X-ray detector which includes a solid-state image pick-up device, and by making the position of the X-ray tube dependent on the static magnetic field of the MR scanner. When interventional techniques are commonly applied in combination with a magnetic resonance imaging device, the organs are suitably visualized, but the instruments were not sufficiently visible. The patent suggests a solution of arranging the X-ray device immediately adjacent to or in the MR device so that the patient does not have to be transported. This latter arrangement in particular is contradictory to considerations of necessity if an attempt were made to use both MR imaging and linear magnetic stereotaxis, where the operation of the two systems within the identical environment at the same time would be completely incompatible.

Framed and frameless systems have thus produced significant advances in neurosurgery. The frameless systems in particular allow the surgeon to apply a probe to the surface of the brain, and then view on a computer monitor the preoperatively imaged, subsurface planes of tissue orthogonal to the axial direction of the probe. This information may have great value to the surgeon, since the display of images correlated to a specific point or region within the brain where the neurosurgeon is working provides a distinct advantage over the simple fixed display of an atlas of the three orthogonal sets of slices as might be shown on a light box on the wall of the operating room.

Recent applications of both framed and frameless stereotaxy systems to surgery have begun to use images that are acquired in real time or close to real time. Exemplary of such applications is U.S. Pat. No. 5,531,520 to Grimson et al., which discloses an image data registration system, wherein a video camera obtains real-time images of patient anatomy which are combined with MR or CT images to provide for enhanced visualization of the anatomic region. U.S. Pat. No. 5,740,802 to Nafis et al. discloses an interactive surgery planning and display system comprising live video of external surfaces of the patient mixed with interactive computer-generated models of internal anatomy obtained from diagnostic imaging of the patient. The computer images and the live video are coordinated and displayed to a surgeon in real time in order to guide surgery. U.S. Pat. No. 5,531,227 to Schneider discloses a method and apparatus for obtaining and displaying in real time an image obtained by one modality such that the image corresponds to a line of view established by another modality. U.S. Pat. No. 5,638,819 to Manwaring and Manwaring discloses a navigational method and apparatus for guiding a surgical instrument to a target location in a body along a specified trajectory in real time.

The prior art generally describes technologies related to matching the coordinates of one imaging system with those of another imaging system. While each invention represents an advancement in the art, they fail to provide for the integrated utilization of MRI and MSS in the same room so as to guide, position, and thereafter monitor in real time the performance of MR-compatible therapeutic devices and instruments within the body without moving the patient from a single gantry. None of the patents or medical and/or scientific journal articles referenced above disclose or suggest the conjoint use of MSS/MRI to effect real-time MR image-guided visualization of MSS-directed surgical or endovascular procedures. The types of combined modality systems which have been discussed previously include ultrasonic wave applicators integrally incorporated with MRI, as in, for instance, U.S. Pat. No. 5,590,653, and live video imaging of a patient mixed and coordinated with medical diagnostic imaging data, as in U.S. Pat. No. 5,740,802. The present invention instead discloses a magnetic neurosurgery apparatus, whereby MSS and MRI are employed conjointly and interactively. U.S. Pat. No. 5,590,653 teaches that the same gantry that transports the patient into the imaging volume of the MR imager can also transport the apparatus for the delivery of an ultrasonic treatment. U.S. Pat. No. 5,255,680 teaches a means of controlling the position of the gantry transporting the patient via signals of microcoils on a medical device positioned within the patient. The present invention discloses a completely different concept, in that the same sliding gantry is used to transport the patient between functionally integrated MSS and MRI systems housed in the same room.

The use of MRI to provide intraoperative imaging guidance is a relatively new concept made feasible by the development of new MRI systems that provide high spatial and temporal resolution imaging in conjunction with multiplanar and volumetric three-dimensional data acquisition, thereby making possible interactive image plane definition to facilitate surgical localization and targeting of, for example, a lesion and improving intraoperative navigation. Intraoperative MR imaging enables the surgeon to noninvasively visualize tissue planes beyond the surface of the tissue under direct visual evaluation during a clinical procedure. Moreover, MR imaging enables differentiation of normal from abnormal tissues, and it can display critical structures such as blood vessels in three dimensions. Thus, high-speed MR-guided therapy offers an improved opportunity to maximize the benefits of minimally invasive procedures in real time.

MR imagers which permit continuous real-time visualization of tissues during surgical and endovascular procedures have already been developed. One type of MR unit designed for image-guided therapy is arranged in a "double-donut" configuration, in which the imaging coil is split axially into two components. U.S. Pat. Nos. 5,410,287, 5,519,372 and 5,565,831 provide illustrative examples of such systems. Imaging studies are performed with this system with the surgeon standing in the axial gap of the magnet and carrying out procedures on the patient. A recent article in the medical literature (P. Black et al., "Development and implementation of intraoperative magnetic resonance imaging and its neurosurgical applications," Neurosurgery, 41:831–842 (1997)) suggests that MR-guided minimally invasive therapy is expected to significantly lower patient morbidity because of reduced post-procedure complications. A second type of high-speed MR imaging system combines high-resolution MR imaging with conventional X-ray fluoroscopy and digital subtraction angiography (DSA) capability in a single hybrid unit. U.S. Pat. No. 5,713,357 to Meulenbrugge et al. describes a version of such a system. Both of these new generations of MR scanners provide frequently updated images of the anatomical structures of interest. This close to real time imaging capability makes it possible to use high-speed MR imaging to observe the effects of specific interventional procedures, such as endovascular catheter tracking and intracranial administration of drug agents to targeted tissues, as disclosed by U.S. patent application Ser. No. 08/857,043.

With MSS, the implant might be used to tow or guide a pliable catheter or other drug delivery device to a targeted intracranial location through the brain parenchyma or via the neurovasculature. U.S. Pat. No. 4,869,247 teaches the method of intraparenchymal magnetic manipulation. U.S. Pat. No. 5,654,864 teaches a method for synthesizing a control algorithm for using an MSS to deliver therapies into the body and the brain in particular, and U.S. Pat. Nos. 5,125,888; 5,707,335; and 5,779,694 disclose the use of nonlinear MSS to maneuver a catheter system within the brain.

With currently used endovascular catheterization techniques, there is generally a compromise between longitudinal and torsional rigidity for advancing and negotiating progressively more tortuous and narrow vascular lumens. As a result of these limitations associations with transarterial and transvenous manual catheterization, there has been growing interest in using magnetic fields to guide catheters through the cerebral vasculature. High-resolution visual images denoting the actual position of the medical device within the brain would be extremely useful to the clinician in maximizing the safety and efficacy of the procedure. The availability of an MR-visible drug delivery device combined with MR-visible drug agents would make it possible to obtain near real-time information on drug delivery during interventional procedures in an intraoperative MR system, as well as for postoperative confirmation of the location of the drug delivery device following a nonlinear magnetic stereotaxis procedure. Drug delivery devices, such as catheters, that are both MR-visible and radiopaque could be monitored by both X-ray fluoroscopy and MR imaging, thus making intraoperative verification of catheter location possible during nonlinear magnetic stereotaxis procedures. U.S. patent application Ser. No. 08/857,043 describes a technology comprising a method for MRI image-guided drug delivery. Active MR visualization of catheters and other interventional probes is achieved by means of radiofrequency microcoils positioned at specific points along the distal axis of the device. Another patent application co-authored by the present co-inventors and others further explores this and related approaches (U.S. patent application Ser. No. 09/131,031. Alternative means of using MR signals to localize and track devices with small coils that are placed within the body are taught by U.S. Pat. Nos. 5,211,165, 5,307,808, 5,318,025 and 5,715,822.

Both MRI and MSS enable image-guided placement of a catheter or medical device at targeted intracranial loci. An important issue in image-guided therapy is the accuracy of the navigational process used to direct the movement of the interventional medical device. The use of light-emitting diode-based optical tracking of rigid surgical instruments in combination with the manipulation of the MRI planes can provide continuous interactive feedback between the surgical maneuvers during a procedure and the corresponding images. When using flexible medical devices, such as catheters and guidewires, miniature coils attached at the distal end enable these devices to be detected deep within tissues, as disclosed by U.S. patent application Ser. No. 08/857,043. With MR coil-based tracking methods, the acquisition and display of the corresponding images can result in either the superimposition of the tips of the instruments on previously acquired images, or real-time images can be taken to establish the position of a particular device.

U.S. patent application Ser. No. 09/131,031, filed on Aug. 7, 1998 describes a method and object for selective intraparenchymal and/or neuroendovascular drug delivery and other concurrent medical treatment of abnormalities of the human central nervous system using nonlinear magnetic stereotaxis combined with magnetic resonance (MR) imaging and/or x-ray guidance.

The present invention describes specific apparatus and procedures for performing processes and apparatus in which medical treatments may be performed within a single theater where magnetic resonance imaging and magnetic stereotaxis are to be used.

SUMMARY OF THE INVENTION

A method for performing medical procedures which combine the use of a magnetic surgery system (MSS) and a magnetic resonance imaging (MRI) system within the totality of a procedure is described. An apparatus and theater where this method may be performed is also described. The types of medical procedures which may be performed include, but are not limited to, all forms of surgery, diagnoses and therapies in which instrumentality may be placed, positioned or repositioned within a patient where direct or indirect (e.g., endoscopic or other optical) visualization may be difficult or impossible. A magnetic surgery system (MSS) is functionally integrated with a magnetic resonance imaging (MRI) system to provide a non-invasive, radiation-free modality for integrated MRI/MSS tracking of an interventional medical device. The tracking may be between two or more target locations within a patient's body or between a portal location and a target location.

An integrated MSS/MRI system (method and apparatus and theater) is provided where a single computer system or CPU provides all major computational and manipulative functions to the data and signals within the performance of all of the apparatus within the MRI and MSS combined system. This is referred to herein as a 'superhost' control system, and may be used to 1) operate both the anatomic real-time MRI data acquisition, 2) overlay MRI and MSS images and integrate at least one of these real images with a projected path through the patient, and 3) run the MSS control system and the MSS itself, thereby minimizing duplication of computational systems and devices otherwise individually required to operate each apparatus separately and/or independently. The superhost control system may also provide control of the movement or motivation of a motor driven support for the patient (e.g., a single motor driven sliding gantry) to physically move a patient between MRI and MSS stations within a single room or attached rooms housing the entire magnetic neurosurgical apparatus. The superhost system also allows for convenient, simplified and cost-effective sharing of image and data files (and other computer related tasks and functions) between the MRI and MSS components of the magnetic neurosurgical apparatus.

The system of the invention may also provide instantaneous or real time updating of the 'road map' of anatomical MRI images of body tissue so that intra-operative biplanar (e.g., X-ray) images of the MSS fluoroscope system are superimposed in register on the most recent MR imaging 'background'.

Another aspect of the present invention is the structural design and function of the operation theater, particularly as a single room wherein the entire MRI/MSS combined system is housed in a single room, which may be magnetically shielded in whole or in part if needed, thereby reducing the cost of separate MRI and MSS rooms as well as physically enabling better communication of a patient back and forth between the two systems as the medical procedure may require.

The present method and apparatus and system inventions are particularly suitable for providing an integrated diagnostic and therapeutic apparatus for MSS/MRI real-time imaging of brain function and heart function during interventional endovascular procedures, particularly where interventional devices such as catheters with different magnetic field and radiologic visibility characteristics are directed sequentially through one or more organs or body parts to perform a diagnostic or therapeutic procedure.

DETAILED DESCRIPTION OF THE INVENTION

The present invention discloses a novel magnetic neurosurgery apparatus, wherein neurosurgical procedures can be performed using a combination of MSS navigational methods and MRI imaging guidance. The present invention discloses a means of integrating the image acquisition, surgeon/operator interface, and control systems for the hybrid interactive utilization of MSS and MRI, wherein said systems interactively carry out target definition, localization, trajectory planning, and verification of the final position of a probe within the target, as well as perform on-line tracking and monitoring of the intervention.

As used herein, "image" means the data that represents the spatial layout of anatomical or functional features of a patient, which may or may not be actually represented in visible graphical form. "Imaging modality" means the method by which an image is obtained, for example, MRI, X-ray, CT. "Fiducial marker" means a feature or object that can be used for image analysis, matching, or registration of images. "Segmentation" is the method of dividing an image into areas which have some physical significance. "Transformation" means processing an image so that it altered according to specified criteria. "Registration" means an alignment process by which two images are positioned coincident with each other so that corresponding points appear in the same position on the registered images. "Probe" means any medical device or instrument, or plurality of said devices or instruments, that are used to deliver image-guided therapy to the human body. "Superhost computer" means the computational system that is used to operate more than one function related to the performance of each of the MRI apparatus and the MSS apparatus. Preferably the superhost or master computational system will perform all aspects of the MSS and MRI, except for subsidiary and localized functions where a single chip might suffice, such as a warning device indicating that a coupling of elements is not correct, or there is a localized leak of material from a transport line, standard patient monitoring systems (e.g., EKG or EEG) or a warning light that a temperature has been exceeded on a distal component. The master computational system may operate either system separately, or in any combined manner. By at least two functions, it is meant that the master computer system will have at least two functions for each unit selected from such functions as receiving electronic data, storing electronic data, treating electronic data (e.g., compressing, expanding, enhancing, comparing, mathematically manipulating, etc.), sending electronic data (e.g., to a monitor, an internet address or host), indicating a change in conditions based upon received or compared data or signals, directing operation of equipment (e.g., altering fields within the MSS to guide a medical device, signaling the gantry or gurney to move, operating the MRI imaging function, and any other computational or operational function which can be practiced or performed by a computer.

The present invention includes an operating theater comprising a) magnetic resonance imaging apparatus having an area within which a patient may be placed for performance of magnetic resonance imaging, b) magnetic stereotaxis or magnetic guidance apparatus having an area within which a patient may be placed for performance of magnetic guidance of medical devices, the operating theater having a support for a patient which can be transported along a path between the area within which a patient may be placed for performance of magnetic resonance imaging and the area within which a patient may be placed for performance of magnetic stereotaxis or magnetic guidance of medical devices, the path moving through a plane with magnetic shielding within the plane between the magnetic resonance imaging apparatus and the magnetic stereotaxis or magnetic guidance apparatus.

The operating theater may have the support for a patient comprising a sled arrangement on tracks between the magnetic resonance imaging apparatus and the magnetic guidance apparatus. The support may, for example, be moved along the tracks by a motor. The magnetic resonance imaging system may have a computer electronically associated therewith which receives data from the magnetic resonance imaging system to create an electronic image. The computer may also be electronically associated with the magnetic stereotaxis or magnetic guidance apparatus so that selected signals to the computer effect a signal from the computer to said magnetic stereotaxis or magnetic guidance apparatus to vary magnetic fields within the magnetic stereotaxis or magnetic guidance apparatus, which magnetic fields are able to guide a medical device. The computer may have the ability to overlay a prospective path for guidance of a medical device by the magnetic guidance apparatus onto said electronic image. The computer may also be electronically associated with the magnetic stereotaxis or magnetic guidance apparatus so that selected signals to the computer effect a signal from the computer to the magnetic guidance apparatus to vary magnetic fields within the magnetic guidance apparatus, which magnetic fields are able to guide a medical device. The magnetic resonance imaging system may have a computer electronically associated therewith which receives data from the magnetic resonance imaging system and operates upon the received data from the magnetic resonance imaging system to create an electronic image.

Another aspect of the present invention comprises a method of performing a medical treatment comprising the steps of obtaining an electronic image of a patient on a support by magnetic resonance imaging and storing the electronic image on a computer, moving a patient while the patient remains on the support to magnetic stereotaxis or magnetic guidance apparatus, the moving being performed on a track which is secured between an apparatus which performs the magnetic resonance imaging and the magnetic stereotaxis or magnetic guidance apparatus, and operating the magnetic stereotaxis or magnetic guidance apparatus with reference to the electronic image or a visual image generated from the electronic image to guide a medical device through the patient. The method may have as the support a gantry or gurney, and said gantry or gurney may move on tracks which are fixed in relationship to the magnetic resonance apparatus and the magnetic stereotaxis or magnetic guidance apparatus. As noted elsewhere, the method may have the electronic image overlaid with a prospective path for guidance of a medical device through the patient. This can be done in many different visualization fashions, such as where a physician views a monitor displaying the electronic image to track progression of a medical device along the prospective path. The physician may determine that actual movement of the medical device deviates by an undesirable amount, so that the physician stops movement of the medical device by the magnetic stereotaxis or magnetic guidance apparatus. Then, after stopping movement of the medical device, the magnetic stereotaxis or magnetic guidance device is operated for at least a period of time in which the physician alters the prospective path by input to the computer. Also, the procedure may includes steps where after said medical device has been guided and moved through said patient by the magnetic stereotaxis or magnetic guidance apparatus, the magnetic stereotaxis or magnetic guidance system is stopped, the patient is returned to the magnetic resonance imaging apparatus while remaining on the support, a second magnetic resonance electronic image is created by the magnetic resonance imaging apparatus, and the position of the medical device within the patient is determined from the second electronic image. Where the physician determines that conditions affected by the medical device are undesirable, the physician stops movement of the medical device by the magnetic stereotaxis or magnetic guidance apparatus.

Some general features of the magnetic neurosurgery apparatus will be described next, with particular regard to the means of integrating the image acquisition, surgeon/operator interface, and control systems for the hybrid interactive utilization of MSS and MRI. It should be understood, however, that specific embodiments of the methods of the invention will depend on the location and accessibility of the lesion or other target within the body, and the nature of the medical probe to be advanced to the target location and the therapeutic or diagnostic procedure to be carried out there. Thus, target definition, localization, trajectory planning, and verification of the final position of a probe within the target, as well as the performance of on-line tracking and monitoring of the intervention, may vary depending on the exact nature of the endovascular, intracerebroventricular, or intraparenchymal procedure (and the location of the target lesion).

Figure 1:
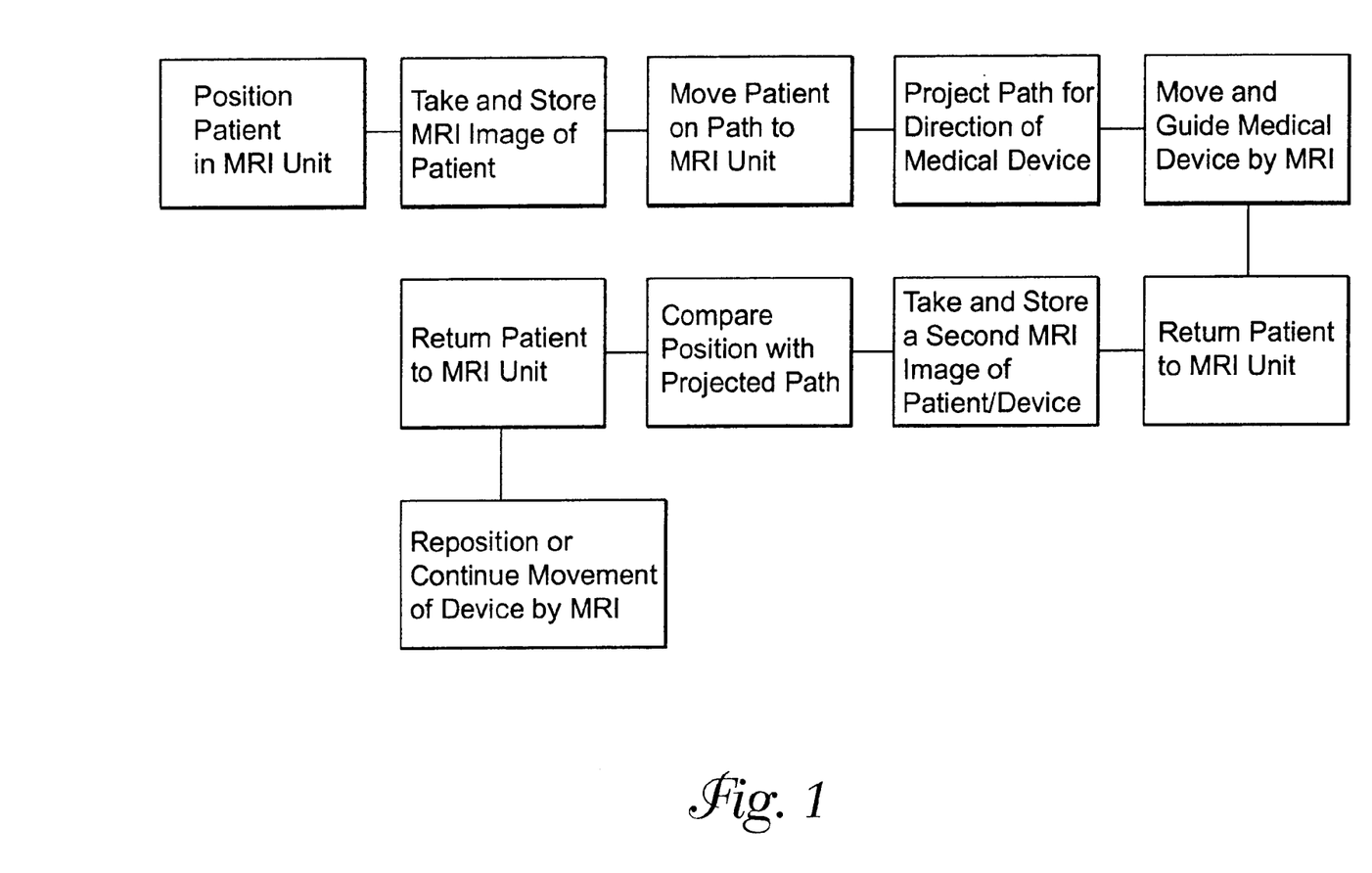
FIG. 1 is a flow diagram outlining one procedure which may be used in the practice of the present invention.

FIG. 1 shows a flow diagram of one route which may be followed in the practice of the present invention. A patient is first positioned within an MRI unit to provide an image which is to be used during the implantation or positioning of a medical device for use in a medical procedure (for treatment or diagnosis). An MRI image is taken and recorded on the master computer system. At this point or after subsequent movement of the patient to the MSS unit, a projected or prospective path of movement of a medical device through the patient is estimated or determined. This prospective path may be created by use of a monitor and responsive light pen or contact pen, joystick, keyboard control, mouse or other directing device, the activity of these instruments on the screen adding data to the MRI image. The data is received by the computer and then overlaid onto the electronic MRI image by the computer. After the patient has been moved to the associated or attached MSS unit, the MRI image with the prospective path is used in the movement of the medical device by the MSS unit. Although the unit may guide and direct the medical device in a fully automatic mode, the system would most often be used in an automatic mode which is monitored by an appropriate medical professional (e.g., surgeon, technician, nurse, etc.) who may interrupt the automatic function and stop or redirect the MSS apparatus, or the image is used completely manually as a road map by the surgeon. After the medical device has been moved at least a significant amount by the MSS apparatus (e.g., at least so far that some additional monitoring may be necessary or desirable), up to and including completion of the entire prospective path of the medical device, the patient is returned to the MRI unit. A second MRI image of the patient and the position of the medical device is taken and stored (storage means at least temporary retention on a hard drive for viewing the image on a monitor and may include a more permanent storage on a disk, cassette or hard drive). The second image is compared with the prospective path, with the medical professionals determining the appropriate course of action (repositioning, retracking a portion of the traversed path, continued advancement of the medical device, initiation of the diagnosis or therapy upon attainment of the proper position by the medical device, etc.). These procedures may be repeated as many times as is necessary to the conclusion of the intended medical procedure.

It should be noted, as mentioned elsewhere herein, that where the MSS procedure uses a medical device with a magnetic element or magnetic responsive element which would interfere with the MRI imaging or which might be moved by the MRI magnetic fields, the magnetic element should be retracted or removed from any portion of the field of the MRI imaging where it would be disadvantageous for the magnetic element to be present. The magnetic element or magnetically responsive element would be replaced to an appropriate position when the MSS procedure was later continued.

Figure 2:
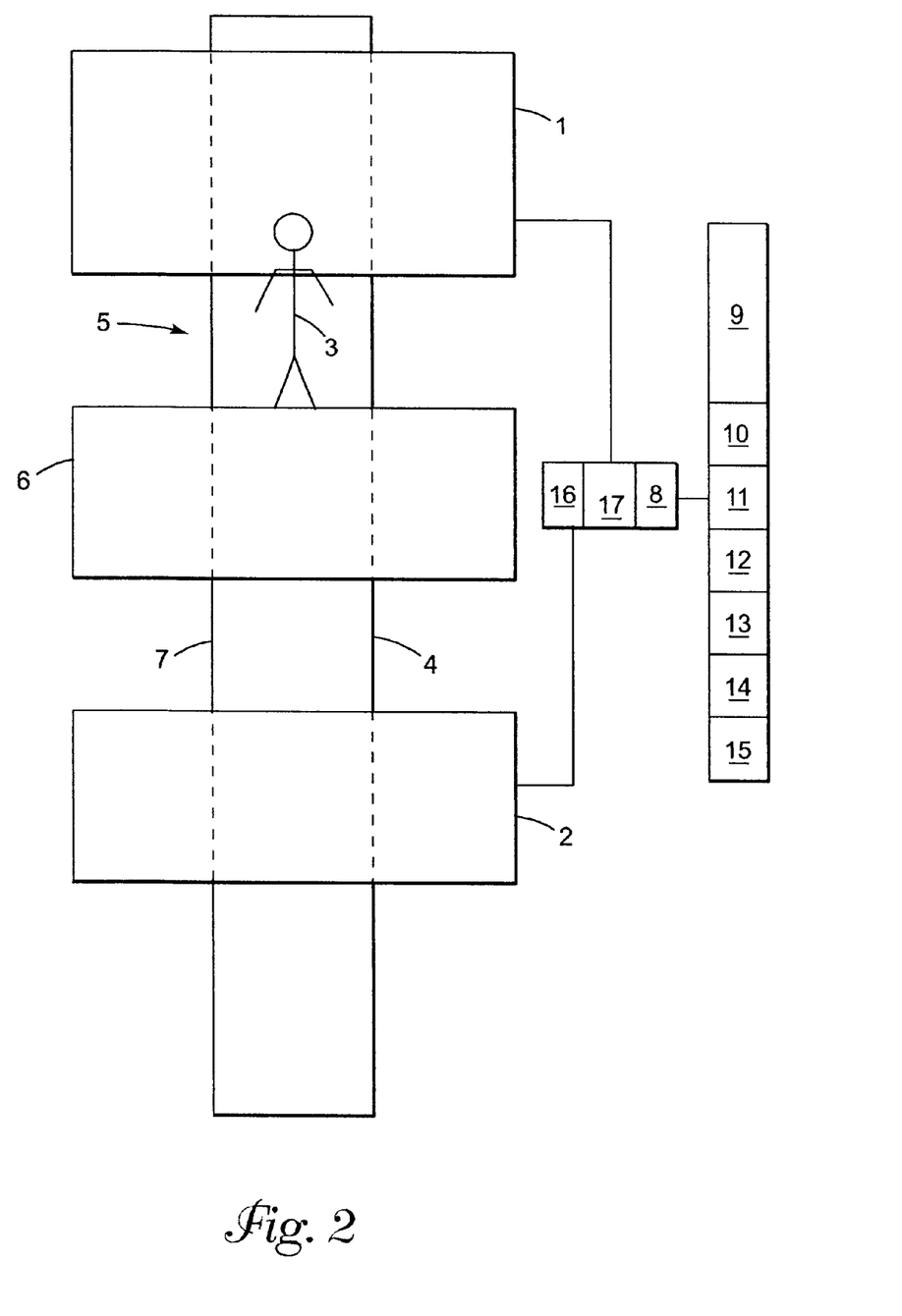
FIG. 2 shows one configuration combining MRI and MSS equipment within a single work space.

FIG. 2 is a schematic representation of the magnetic neurosurgery apparatus showing the relationship of the MRI 1 and MSS 2 components. A patient 3 requiring an image-guided therapeutic intervention is placed on a sliding gantry 4 in the room housing the magnetic neurosurgery apparatus. A patient undergoes a high-resolution MR scan of the brain or other target tissue to anatomically localize in 3D the location of the target tissues requiring image-guided treatment utilizing a medical probe. The resulting high-resolution 3D MR image is automatically segmented to produce enhanced visualization of the anatomy of the target lesion and the surrounding tissues. The imaging data is also registered to the patient's anatomy so that trajectories for advancing and placing the medical probe can be defined, and so that the position of the device within the patient can be depicted on displayed images.

A first surgical pit 5 may be provided outside of the MRI imaging system 1, along the path of the gurney 4. Other doagnostic or therapeutic stations may be located at various sites between the MSS 2 and the MRI 1 systems. Shown merely for purposes of example, without limitation as to the type or number of procedures and their location within the total system, FIG. 2 shows a separate apparatus 6 between the MRI system 1 and the MSS system 2 which could be a laser surgery station, cryogenic station (e.g., with liquid helium or liquid nitrogen), or any other medical diagnostic or therapeutic apparatus. A full body surgical pit 7 may also be provided within the system. Such variations, alternatives and design changes, once the fundamentals of the system have been disclosed by this patent to the ordinarily skilled artisan, are apparent.

A fundamental requirement for MR monitoring of therapeutic interventions is implementation of MR pulse sequences with appropriate spatial and temporal resolution. For monitoring purposes, several MR sequences are known in the art that have adequate temporal resolution to be useful with the present invention. Preferred are pulse sequences such as fast spin echo pulse sequences, various gradient echo pulse sequences, and echo-planar pulse sequences, which produce reasonably high-resolution images with a short (<1 second) acquisition time.

The MR images are automatically transferred to the superhost computer 8 and thereafter used to control the MSS in real time or near real time. The MR images are preferably computed using a recursive formulation of the correlation method, such as, for example, described by Cox et al. (*Magn. Reson. Med.*, 33:230–236 (1995)), wherein multiple linear regression of the voxel time series is performed against known reference waveforms, thereby producing up-to-date MR images within 1 second of data acquisition. In the MR imaging method described by Cox et al., data are acquired at $1^6$ 16-bit samples/second for all pulse sequences, and are digitally filtered and subsampled to the desired bandwidth before reconstruction. The amount of CPU time spent is proportional to the number of raw data points, such that a 64×64 image matrix typically takes 80–100 milliseconds and a 128×128 image matrix typically takes 200–400 milliseconds. The widespread availability of high speed, high precision A/D converters and low inductance local gradient coils makes it possible to perform real-time imaging and reconstruct an entire region of anatomy, such as the brain, in a few seconds.

In the method of the present invention, the MR images also provide 3-D information about the initial position of the probe on the surface of the body relative to the target lesion. The MRI data is automatically entered into the MSS superhost computer 8 interface to instruct the system how far, how fast and in what step sizes to move the probe. This can be done by using cursor cross hairs, screen contact pencils, virtual drawing system, mouse, or other graphic or viewable drafting systems that show the location of the probe tip on a computer screen superimposed on the most recently acquired MR image. The surgeon then enables the computer to instruct the MSS system to execute the required incrementally-stepped movement of the probe tip by using its control algorithm to produce magnetic fields that steer the magnetic tip of the probe. Biplanar fluoroscopic images are obtained during the movement sequence to localize the new position of the tip of the probe as it is advanced towards the target. The resulting X-ray information is automatically sent to the superhost computer 8, wherein instant updating against the 'road map' of anatomical MR images of body tissues is performed, such that intraoperative biplanar X-ray images of the MSS fluoroscope system are superimposed and registered on the MR imaging 'background.'

The operation of the magnetic neurosurgery apparatus is controlled from an operator console 9, which includes a keyboard and control panel 10 and a display 11. The console 91 communicates with the superhost computer 8 to enable an operator (not shown) to control the display of images on the screen 11. The superhost computer may include a number of modules, including and image processing module 12, a CPU module 13, and a memory module 14 to integrate the operation of the MRI system 1 and the MSS 2 components. The operator console 9 is also linked to the superhost computer 8 by way of a pulse generatior module 15 to operate the system components so as to carry out the correct MRI scan sequence. The superhost computer is also connected to a patient data controller 16 which received physiological signals from the patient, such as EKG and ECG signals, during patient imaging and treatment. The superhost computer 8 controls a patient positioning module 17 to move the patient to the desired location for MRI or MSS procedures.

The magnetic neurosurgery apparatus is preferably used in conjunction with medical probes, such as the drug delivery device disclosed in a U.S. patent application Ser. No. 09/130,031 entitled "MR-visible Medical Device for Neurological Interventions Using Nonlinear Magnetic Stercotaxis and Method for MR Imaging or X-ray Visualization." The MR-visible drug delivery probe is navigated by MSS to the target tissue and/or advanced into the patient via endovascular, intracerebroventricular, or intraparenchymal entry ports based on the most recently acquired (e.g., real-time or near real-time) MRI data in the superhost computer. In one particularly preferred embodiment of the present invention, a plurality of medical probes, each with an MSS-responsive magnetic tip disposed at the distal end, are sequentially guided by MSS to targeted locations in the cerebral vasculature, ventricles or parenchyma. As each probe is positioned at the appropriate MRI-determined target location, its MSS-responsive magnetic tip is retracted or otherwise deactivated magnetically, thereby rendering the probe insensitive to the MSS magnetic fields during placement of the next probe. Said medical probes preferably have a linearly arranged array of radiopaque and MR-visible markers disposed at the distal end to provide easily identifiable reference points for trackability and localization under MR imaging and X-ray fluoroscopy guidance. Additionally, active MR visualization of the medical probe is achieved or enhanced by means of RF microcoils disposed along the distal axis of the probe. MR visibility can be variably adjusted based on requirements related to degree of signal intensity change for probe localization and positioning, enhancement along the shaft of the probe, enhancement around the body of the probe, visibility of the proximal and distal ends of the probe, degree of increased background noise associated with probe movement, and other factors which either increase or suppress noise and artifacts associated with the probe. It should be understood, however, that the image registration method and apparatus of the present invention, although emphasized with respect to endovascular procedures, is not limited to endovascular procedures, but may also be used for intracranial, transcavitary and other procedures in all other regions of the body.

A method of performing a diagnostic or therapeutic procedure comprising obtaining an electronic image of a patient on a support by magnetic resonance imaging and storing said electronic image on a computer, moving said patient through a plane with magnetic shielding within said plane between said magnetic resonance imaging apparatus and said magnetic stereotaxis or magnetic guidance apparatus while said patient remains on said support to magnetic stereotaxis or magnetic guidance apparatus, said moving being performed on a track which is secured between an apparatus which performs said magnetic resonance imaging and aid magnetic stereotaxis or magnetic guidance apparatus, and operating said magnetic stereotaxis or magnetic guidance apparatus with reference to said electronic image or a visual image generated from said electronic image to guide a medical device through said patient.

What is claimed:

1. An operating theater comprising
   a) magnetic resonance imaging apparatus having an area within which a patient may be placed for performance of magnetic resonance imaging,
   b) magnetic stereotaxis or magnetic guidance apparatus having an area within which a patient may be placed for performance of magnetic guidance of medical devices,
   said operating theater having a support for a patient which can be transported along a path between said area within which a patient may be placed for performance of magnetic resonance imaging and said area within which a patient may be placed for performance of magnetic stereotaxis or magnetic guidance of medical devices, said path moving through a plane with magnetic shielding within said plane between said magnetic resonance imaging apparatus and said magnetic stereotaxis or magnetic guidance apparatus.

2. The operating theater of claim 1 wherein said support for a patient comprises a support arrangement on tracks between said magnetic resonance imaging apparatus and said magnetic guidance apparatus.

3. The operating theater of claim 2 wherein said support is moved along said tracks by an MR-compatible motor.

4. The operating system of claim 1 wherein said magnetic resonance imaging system has a computer electronically associated therewith which receives data from said magnetic resonance imaging system to create an electronic image.

5. The operating system of claim 4 wherein said computer is also electronically associated with said magnetic stereotaxis or magnetic guidance apparatus so that selected signals or instructions to said computer effect a signal from said computer to said magnetic stereotaxis or magnetic guidance apparatus to vary magnetic fields within said magnetic stereotaxis or magnetic guidance apparatus, which magnetic fields are able to guide a medical device.

6. The operating system of claim 4 wherein said computer has the ability to overlay a prospective path for guidance of a medical device by said magnetic guidance apparatus onto said electronic image.

7. The operating system of claim 6 wherein said computer is also electronically associated with said magnetic stereotaxis or magnetic guidance apparatus so that selected signals to said computer effect a signal from said computer to said magnetic guidance apparatus to vary magnetic fields within said magnetic guidance apparatus, which magnetic fields are able to guide a medical device.

8. The operating system of claim 1 wherein said magnetic resonance imaging system has a computer electronically associated therewith which receives data from said magnetic resonance imaging system and operates upon said received data from said magnetic resonance imaging system to create an electronic image.

9. A method of performing a diagnostic or therapeutic procedure comprising obtaining an electronic image of a patient on a support by magnetic resonance imaging and storing said electronic image on a computer, moving said patient through a plane with magnetic shielding within said plane between said magnetic resonance imaging apparatus and said magnetic stereotaxis or magnetic guidance apparatus while said patient remains on said support to magnetic stereotaxis or magnetic guidance apparatus, said moving being performed on a track which is secured between an apparatus which performs said magnetic resonance imaging and aid magnetic stereotaxis or magnetic guidance apparatus, and operating said magnetic stereotaxis or magnetic guidance apparatus with reference to said electronic image or a visual image generated from said electronic image to guide a medical device through said patient.

10. The method of claim 9 wherein said support is a gantry or gurney, and said gantry or gurney moves on tracks which are fixed in relationship to said magnetic resonance apparatus and said magnetic stereotaxis or magnetic guidance apparatus.

11. The method of claim 9 wherein said electronic image is overlaid with a prospective path for guidance of a medical device through said patient.

12. The method of claim 11 wherein a physician views a monitor displaying said electronic image to track progression of a medical device along said prospective path.

13. The method of claim 12 wherein when said physician determines that actual movement of said medical device deviates by an undesirable amount, said doctor stops movement of said medical device by said magnetic stereotaxis or magnetic guidance apparatus.

14. The method of claim 13 wherein after discontinuing movement of said medical device, said magnetic stereotaxis or magnetic guidance device is operated for at least a period of time in which said physician alters the prospective path by input to said computer.

15. The method of claim 9 wherein after said medical device has been guided and moved through said patient by said magnetic stereotaxis or magnetic guidance apparatus, said magnetic stereotaxis or magnetic guidance system is stopped, said patient is returned to said magnetic resonance imaging apparatus while remaining on said support, a second magnetic resonance electronic image is created by said magnetic resonance imaging apparatus, and the position of the medical device within said patient is determined from said second electronic image.

16. The method of claim 12 wherein when said physician determines that conditions affected by said medical device are undesirable, said physician discontinues movement of said medical device by said magnetic stereotaxis or magnetic guidance apparatus.

17. The method of claim 9 wherein after guiding a medical device through said patient, the magnetic resonance imaging system is used to monitor the flow of an MR viewable agent introduced into tissue of the patient.

18. The method of claim 17 wherein the magnetic resonance imaging system is used to monitor the flow of a bioactive agent through tissue of the patient in real time.

19. The method of claim 18 wherein said medical device is guided through the brain of a patient and said MR viewable agent is selected from the group consisting of a diagnostic agent and a therapeutic agent.

* * * * *

UNITED STATES PATENT AND TRADEMARK OFFICE
CERTIFICATE OF CORRECTION

PATENT NO. : 6,298,259 B1
DATED : October 2, 2001
INVENTOR(S) : John Kucharczyk and George T. Gillies Page 1 of 1

It is certified that error appears in the above-identified patent and that said Letters Patent is hereby corrected as shown below:

<u>Title page,</u>
Item [73], Assignee, please insert:

-- Regents of the University of Minnesota, Minneapolis, MN (US) and University of Virginia Patent Foundation, Charlottesville, Virginia (US) --

Signed and Sealed this

First Day of April, 2003

JAMES E. ROGAN
*Director of the United States Patent and Trademark Office*